United States Patent [19]

South et al.

[11] Patent Number: 5,559,080
[45] Date of Patent: Sep. 24, 1996

[54] 3-PHENOXYPYRIDAZINES, HERBICIDAL COMPOSITIONS AND USES THEREOF

[75] Inventors: Michael S. South, St. Louis; Michael J. Miller, Manchester, both of Mo.

[73] Assignee: Monsanto Company, St. Louis, Mo.

[21] Appl. No.: 321,069

[22] Filed: Oct. 11, 1994

[51] Int. Cl.$^6$ .................. A01N 43/58; C07D 237/14; C07D 237/16; C07D 237/22
[52] U.S. Cl. .................. 504/238; 504/236; 504/237; 544/229; 544/239; 544/240; 544/241
[58] Field of Search ............... 544/224, 229, 544/239, 240, 241; 504/236, 237, 238

[56] References Cited

U.S. PATENT DOCUMENTS 3,547,617  12/1970  Tamura et al. ................ 544/239
3,652,257  3/1972  Johima ........................ 544/239

FOREIGN PATENT DOCUMENTS 264575  11/1988  Japan ......................... 544/241

OTHER PUBLICATIONS

Jojima et al, *Chemical Abstracts*, vol. 79, No. 14311 (1973).
Ishikawa et al, *Chemical Abstracts*, vol. 75, No. 76709 (1971).

*Primary Examiner*—Emily Bernhardt
*Attorney, Agent, or Firm*—Grace L. Bonner; Joan Thierstein; Dennis R. Hoerner, Jr.

[57] ABSTRACT

Disclosed are certain 3-phenoxypyridazines, compositions thereof which are herbicidal and methods of using such compositions for controlling undesired plants. Intermediate compounds useful in preparing the phenoxypyridazines are also disclosed.

5 Claims, No Drawings

3-PHENOXYPYRIDAZINES, HERBICIDAL COMPOSITIONS AND USES THEREOF

FIELD OF THE INVENTION

The present invention relates to novel compounds useful for controlling undesired plants and for retarding plant growth. More particularly, the present-invention relates to certain 3-phenoxypyridazines useful for controlling undesired plants and for retarding plant growth.

PRIOR ART

In U.S. Pat. No. 4,623,376, certain substituted 3-phenoxypyridazines have been disclosed as being useful as herbicides.

In Auer et al, "The Chemistry and Properties of New and Herbicidal Derivatives of 3-Phenylpyridazine", *Environ. Qual. Saf. Suppl.*, (1975), pp 680–685, certain substituted 3-phenylpyridazines have been disclosed as being useful as herbicides.

There is a continuing need in the art for herbicides which provide a broad spectrum of control of weeds and which may be better tolerated by crops. The present invention produces such kind of improved and useful herbicides.

SUMMARY OF THE INVENTION

The novel compounds of the present invention may be depicted by the following structural formula (K):

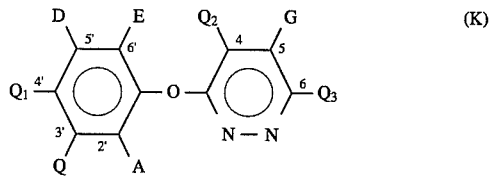

wherein A and E are independently hydrogen, $C_1$–$C_3$ haloalkyl, halo, hydroxycarbonyl or $C_1$–$C_{10}$ alkyl ester thereof, $C_1$–$C_{10}$ alkyl, or $C_1$–$C_{10}$ alkoxy;

$Q_1$ is hydrogen, halo, $C_1$–$C_{10}$ alkoxy, $C_1$–$C_3$ haloalkyl or nitro;

Q and D are independently hydrogen, $C_1$–$C_3$ haloalkyl, halo, $C_1$–$C_{10}$ alkoxy, nitro, tri($C_1$–$C_3$ alkyl) silyl, $C_1$–$C_{10}$ alkyl, or $C_1$–$C_3$ haloalkoxy;

$Q_2$ is hydrogen, halo, $C_1$–$C_{10}$ alkyl, or $C_1$–$C_3$ haloalkylphenoxy;

G is hydrogen, $C_1$–$C_{10}$ alkoxy, $C_1$–$C_{10}$ alkylthio, $C_1$–$C_{10}$ alkylamino, $C_1$–$C_3$ haloalkylphenoxy, hydroxy, $C_1$–$C_3$ haloalkoxy, $C_1$–$C_{10}$ alkyl or phenylthio;

$Q_3$ is hydrogen, halo, $C_1$–$C_{10}$ alkyl, or $C_1$–$C_{10}$ alkoxy;

A and Q or Q and C optionally forming part of a fused second aromatic six membered hydrocarbon ring; and either nitrogen of the pyridazine ring optionally being substituted with an oxide.

The present invention provides novel compounds of the general Formula K depicted above which exhibit desirable herbicidal properties and further provides herbicidal compositions for the selective controlling of weeds in crop plants. The compositions comprise one or more compounds of Formula K herein by themselves or admixed with one or more carriers, such as solid and/or liquid inert extenders or diluents and/or wetting agents and optionally other active herbicides, insecticides, growth regulators, plant nutrients and like additaments. The invention also provides an effective method of controlling undesirable plants, such as grasses, perennial and annual broad-leafed weeds and so on which comprises applying to the locus of the plants to be controlled in a herbicidal effective amount of at least one 3-phenoxy pyridazine compound.

These novel 3-phenoxy pyridazine compounds which may be employed as an active ingredient in this invention can be prepared by a variety of processes such as one of the general procedures as will be described below.

The present invention also provides new and useful processes for making 3-phenoxypyridazine compounds and intermediates thereof.

DETAILED DESCRIPTION OF THE INVENTION

It has been shown that the phenoxy substituted pyridazine compounds within the above depicted general Formula K are not only herbicidal but also have good herbicidal tolerance by certain crop plants, especially corn. The preferred compounds herein provide a broader spectrum of weed control and show good perennial broad-leaf activity. The field soil half-life of the preferred compounds provides longer residual control than alachlor but is normally short enough that any carryover problems are environmentally acceptable.

In this specification and claims, numerical values are not critical unless otherwise stated. That is, the numerical values may be read as if prefaced with the word "about" or "substantially".

The following defines the various terms used in the application.

The term "$C_1$–$C_7$ alkyl" or in the shortened cognate form "$C_1$–$C_7$ alk" as used herein include the straight and branched aliphatic groups of one to ten carbon atoms, such as methyl, ethyl, propyl, isopropyl (1-methyl-ethyl), butyl, isobutyl, (2-methylpropyl), sec-butyl, (1-methylpropyl), tert-butyl, (1,1-dimethylethyl), pentyl, isopentyl, (3-methylbutyl), sec-pentyl (1-methylbutyl), 1,1-dimethylpropyl, 1-2-dimethylpropyl, neopentyl, (2,2-dimethylpropyl), hexyl, isohexyl (4-methylpentyl), sec-hexyl, (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl,1,1,2-trimethylpropyl,1,1,2-trimethylpropyl and the like. The terms, such as "$C_1$–$C_3$" and $C_1$–$C_5$" are included in the term $C_1$–$C_{10}$ but with a corresponding lesser number of carbon atoms as indicated.

The term "$C_1$–$C_3$ haloalkyl" as used herein includes such radicals as trifluoromethyl, trichloromethyl, difluoromethyl, chlorodifluoromethyl, fluoromethyl, bromomethyl, α,α-difluoroethyl, pentafluoroethyl, heptafluoro-n-propyl, pentachloroethyl, iodomethyl, etc., where the number of carbon atoms in the alkyl is 1-3, inclusive.

The term "halogen" either alone or in compound words such as "haloalkyl" denotes fluorine, chlorine, bromine or iodine.

The term "alkoxy" denotes methoxy, ethoxy, n-propyloxy, isopropyloxy and the different butoxy, pentoxy, hexyloxy isomers, etc.

Processes for preparing the compounds of the present invention are disclosed in the schematic diagrams and written descriptions which follow below.

In broad aspect, the preferred overall process for preparing the compounds of Formula K is best viewed in the separate process steps required to prepare the necessary intermediates, immediate precursors and end products of the above formula. The products of "Processes I and II", provide the intermediates necessary for "Process III". The compounds according to Formula K are prepared by either a single process "III" or any suitable combination of "Processes I–III". It is expressly understood that various modifications obvious to those skilled in the art are contemplated. Specific embodiments of the preparation of the compounds herein are described in Examples 1–5 below.

In the sequence of process steps described below,

X is selected from substituents A, Q, $Q_1$, D and E as defined above,

Y is selected from substituents $Q_2$, G and $Q_3$ as defined above, m is zero or an integer of 1–5 inclusive, and n is zero or an integer of 1–3, inclusive.

PROCESS I

This process describes the preparation of important intermediate compounds of Formula F which are useful in the overall process scheme for producing compounds of Formula K.

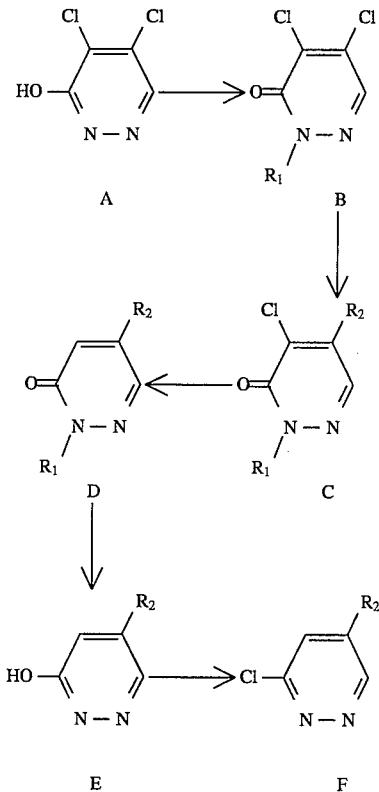

The first step in the process for the preparation of compounds of Formula F proceeds from 4,5-dichloro-3-hydroxypyridazine A, which is commercially available and known in the art. Treatment of A with an appropriate protecting group chosen from chloromethylmethyl ether, chloromethylthiomethyl ether, dihydropyran, or 2-methoxyethoxymethyl chloride and an organic or inorganic acid such as p-toluenesulfonic acid or sulfuric acid or a base chosen from triethylamine or N,N-diisopyropylethylamine gives a compound of Formula B. In compounds of Formula B, $R_1$ is derived from one of the protecting groups mentioned above. The reaction can be carried out in any anhydrous solvent or mixture of solvents with the preferred solvents being chosen from ether, tetrahydrofuran, benzene, toluene, or methylene chloride. The reaction temperatures may range from –78° C. to 150° C., preferably 0° C. to 100° C. The reaction period may be chosen from a few minutes to several weeks depending on the amounts of reagents, reaction temperature, etc. After the reaction is complete, the mixtures containing the compounds of Formula B are diluted with an appropriate organic solvent and extracted with an aqueous base such as sodium bicarbonate. The compounds of Formula B are isolated by drying the organic solvent, filtration and then removal of the solvent in-vacuo. The compounds of Formula B are utilized as is or if necessary the product is purified by standard methods such as crystallization or column chromatography.

The second step in Process I involves the conversion of compounds of Formula B to C by treatment of B with an alkyl alcohol, thiol, or amine and an appropriate base such as sodium hydroxide, potassium hydroxide, sodium hydride, potassium hydride, sodium bicarbonate, potassium carbonate, triethyl amine, N,N-diisopropylethylamine, or DBU to give compounds of Formula C. In compounds of Formula C, $R_2$ is derived from the alkyl alcohol, thiol or amine mentioned above and in many cases would be equivalent to $Y_n$ of Formula K. The reaction can be carried out neat with the above mentioned alcohol, thiol, or amine as solvent or in any anhydrous solvent or mixture of solvents with the preferred solvents being chosen from ether, tetrahydrofuran, benzene, N,N-dimethylformamide, or dimethylsulfoxide. The reaction temperatures may range from –78° C. to 150° C. preferably –20° C. to 100° C. The reaction period may be chosen from a few minutes to several weeks depending on the amounts of reagents, reaction temperature, etc. The mixtures containing the compounds of Formula C are then diluted with an organic solvent and extracted several times with water. The compounds of Formula C are isolated by removal of the organic solvent in-vacuo and may be used as is or if necessary may be purified by standard methods, such as crystallization or column chromatography.

The third step in Process I involves the conversion of compounds of Formula C to D by treatment of C with hydrogen, an appropriate transition metal catalyst such as Pd-C, Pt-C or $Pt_{O2}$, and an appropriate base such as triethyl amine, N,N-diisopyropylethylamine, or DBU to give compounds of Formula D. The reaction can be carried out in any anhydrous solvent or mixture of solvents with the preferred solvents being chosen from methanol, ethanol, benzene or ethyl acetate, preferably methanol or ethanol. The reaction temperature may range from –78° C. to 150° C., preferably 0° C. to 40° C. The reaction period may be chosen from a few minutes to several weeks depending on the amounts of reagents, reaction temperature, etc. The compounds of Formula D are isolated by filtration and removal of the solvent in-vacuo. The compounds of Formula D are used as is or may be purified by standard methods, such as crystallization or column chromatography.

The fourth step in Process I involves the conversion of compounds of Formula D to compounds of Formula E by treatment of D with an aqueous acid such as hydrochloric acid, phosphoric acid, sulfuric acid or nitric acid to give compounds of Formula E. The reaction is carried out in the aqueous acid as solvent in the presence of a co-solvent such as methanol, ethanol or tetrahydrofuran with the reaction temperatures ranging from 0° C. to 100° C. preferably 25° C. to 100° C. The reaction period may be chosen from a few minutes to several weeks depending on the amounts of reagents, reaction temperature, etc. The compounds of Formula E are isolated by making the reaction mixture basic with sodium hydroxide, extracting with a chlorinated solvent such as methylene chloride, chloroform, or carbon tetrachloride to remove contaminants then acidifying with concentrated acid to precipitate the product. The products of Formula E are then collected by filtration and dried and may be used as is or if necessary purified by standard methods, such as crystallization or column chromatography.

The fifth step in Process I involves the conversion of compounds of Formula E to F by treatment of E with a chlorinating agent such as thionyl chloride, oxalyl chloride, sulfuryl chloride, or phosphorus oxychloride to give compounds of Formula F. The reaction is carried out neat in the chlorinating agent as solvent or with the chlorinating agent and a co-solvent such as methylene chloride, chloroform or carbon tetrachloride. The reaction temperature may range from 0° C. to 100° C., preferably 25° C. to 100° C. The reaction period may be chosen from a few minutes to several weeks depending on the amounts of reagents, reaction temperature, etc. The compounds of Formula F are isolated by removal of the solvents in-vacuo to give the products which can be used as is or purified by standard methods, such as crystallization or column chromatography.

PROCESS II

This process describes the preparation of important intermediate compounds of Formula H which are useful in the overall process scheme for producing compounds of Formula K.

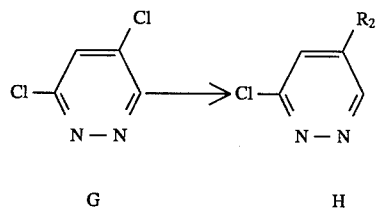

G    H

The first step of Process II involves the conversion of 3,5-dichloropyridazine G which is known in the art (W. Deinhammer et. al., German Pat. No. 2,706,701, 1978), to compounds of Formula H by treatment with one equivalent of an alkyl alcohol, thiol, or amine and an appropriate base, such as sodium hydroxide, potassium hydroxide, sodium hydride, potassium hydride, sodium bicarbonate, potassium carbonate, triethyl amine, N,N-diisopropylethylamine, or DBU. In compounds of Formula H, $R_2$ is derived from the alkyl alcohol, thiol or amine mentioned above and in many cases would be equivalent to $Y_n$ of Formula K. The reaction can be carried out neat with the above mentioned alcohol, thiol or amine as solvent or in any anhydrous solvent or mixture of solvents with the preferred solvents being chosen from ether, tetrahydrofuran, benzene, N,N-dimethylformamide or dimethylsulfoxide. The reaction temperatures may range from –78° C. to 150° C., preferably –20° C. to 100° C. The reaction period may be chosen from a few minutes to several weeks depending on the amounts of reagents, reaction temperature, etc. The mixtures containing the compounds of Formula H are then diluted with an organic solvent and extracted several times with water. The compounds of Formula H are isolated by removal of the organic solvent in-vacuo and may be used as is or if necessary may be purified by standard methods, such as crystallization or column chromatography.

PROCESS III

This process describes the preparation of compounds of Formula K. Phenols of Formula I and pyridazines of Formula J, which are either known in the art, commercially available, or prepared as described herein, are combined together with an appropriate base chosen from sodium hydride, potassium hydride, sodium bicarbonate, potassium carbonate, triethyl amine, N,N-diisopropylethylamine, 2,6-lutidine, or DBU, and optionally an appropriate catalyst chosen from $TiCl_4$, $SnCl_2$, $FeCl_3$, CuCl, CuBr, $AgBF_4$ or CuF to give compounds of Formula K. In these cases $X_m$ and $Y_n$ are defined as given above for Formula K. The reaction may be carried out in any anhydrous solvent or mixture of solvents, preferably ether, tetrahydrofuran, N,N-dimethylformamide, dimethyl sulfoxide, diglyme, glyme, sulfolane, benzene, toluene or xylene. The reaction temperatures may range from –78° C. to 180° C., preferably 0° C. to 150° C. The reaction period may be chosen from a few minutes to several weeks depending on the amounts of reagents, reaction temperature, etc. The products of Formula K are isolated by diluting the reaction mixture with an organic solvent and extracting with water. The organic solvent is then removed in-vacuo and the products of Formula K are either used as is or purified by standard methods, such as crystallization or chromatography, etc.

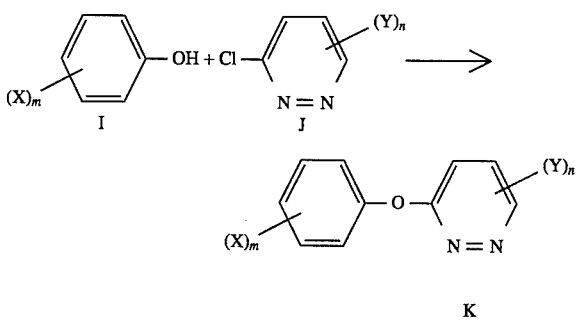

The acid addition salts useful in the present composition can be prepared by admixing a suitable compound of Formula K with a suitable acid to form the corresponding acid addition salt. Examples of those acids which may be employed include inorganic acids, such as hydrochloric acid, sulfuric acid, nitric acid, phosphoric acid and an organic acid such as, trichloroacetic acid. It is to be noted that certain compounds of Formula K cannot be converted conveniently to a suitable corresponding acid addition salt.

Preparation of some of the intermediates of the compounds of this invention and the compounds of this invention are illustrated by the following examples. In the examples which follow, all percentages are given on a weight basis unless otherwise indicated.

EXAMPLE 1

This example describes the preparation of 3-chloro-5-methoxypyridazine which is used as an intermediate in Process III and is a specific embodiment of Process I.

A. 4,5-Dichloro-3-hydroxypyridazine (3000 g, 18.18 moles), dihydropyran (1943 g, 23.08 moles), p-toluenesulfonic acid monohydrate (283 g, 1.49 moles) and 16 L of tetrahydrofuran were added to a 50 L round bottomed flask equipped with a heating mantle, reflux condenser and a mechanical stirrer. The mixture was stirred at reflux for 29 h. Additional dihydropyran was added at 6 h (1328 g, 15.79 mol) and at 21 h (780 g, 9.25 mol). The reaction mixture was allowed to cool to room temperature overnight. The mixture was concentrated in-vacuo to an oily residue. The residue was taken up in 16 L of ethyl acetate and washed with 2N-NaOH (2×6 L). The organic solution was dried (MgSO$_4$) and concentrated in-vacuo to give 4,5-dichloro-2-(tetrahydro-2H-pyran-2-yl)-3(2H)-pyridazinone which was a black oily solid which was used without further purification in the next step. The product was purified by filtration through silica gel with ethyl acetate followed by evaporation and recrystallization from ethyl acetate/cyclohexane to give a white solid, mp=74°–76° C.

Anal. Calc. for C$_9$H$_{10}$N$_2$O$_2$Cl$_2$-0.1 C$_6$H$_{12}$: C, 44.78; H, 4.38; N, 10.89 Found: C, 44.63; H, 4.22; N, 10.94 B. 4,5-Dichloro-2-(tetrahydro-2H-pyran-2-yl)-3(2H)-pyridazinone from the previous step and 17 L of methanol were added to a 50 L round bottomed flask equipped with a glycol cooling jacket and a mechanical stirrer. The resulting solution was cooled to 0° C. and 87% KOH (1172 g, 18.17 moles) was added in portions over approximately 1 h. The mixture exothermed to 40° C. Following the addition the mixture was allowed to stir an additional 3 h at ambient temperature. The reaction mixture was partitioned with 12 L of ethyl acetate and 12 L of H$_2$O. The aqueous layer was extracted with ethyl acetate (2×4 L). The combined organic layers were washed with brine (2×10 L) and dried (MgSO$_4$). The organic solution was clarified by filtration and concentrated to give a dark semi-solid. The crude material was equally divided and added to two 22 L flasks. The material was suspended in 12 L hexanes/ethyl ether (2:1 ratio). The washed material was vacuum filtered on a Buchner funnel and air dried overnight to give 3,406 g (77% over 2 steps) of 4-chloro-5-methoxy-2-(tetrahydro-2H-pyran-2-yl)-3(2H)-pyridazinone as a dark tan solid suitable for further transformations. The product was purified by recrystallization from ethyl acetate/cyclohexane to give a white solid, mp=118° C.–120° C. Anal. Calc. for C$_{10}$H$_{13}$N$_2$O$_3$Cl: C,49.09; H,5.36; N,11.45 Found: C,49.04; H, 5.38; N, 11.43 C. 4-Chloro-5-methoxy-2-(tetrahydro-2H-pyran-2-yl)-3(2H)-pyridazinone (2486 g, 10.16 moles), ethanol (8L), triethylamine (2L, 14.23 moles) and 5% Pd-C (100 g of 50% water-wet Pd-C) were added to a 0.019 stere autoclave. The mixture was hydrogenated at 345–414 kilo Pascals of H$_2$ and heated to a maximum temperature of 43° C. After 24 h, the reaction was complete. The reaction mixture was diluted with a small amount of water and vacuum filtered through celite. The aqueous phase was extracted with ethyl acetate (2×2 L). The combined organics were washed with 5 L brine, dried (MgSO$_4$), and vacuum filtered. The solution was concentrated in-vacuo to give 2133 g (100% yield) of 5-methoxy-2- (tetrahydro-2H-pyran-2-yl)-3(2H)-pyridazinone as a dark oil which later crystallized to give a tan product suitable for further transformations. The product was purified by recrystallization from ethyl acetate/cyclohexane to give a white solid, mp=76° C.–78° C.

Anal. Calc. for C$_{10}$H$_{14}$N$_2$O$_3$: C, 57.13; H, 6.71; N, 13.32 Found: C, 56.86; H, 6.61; N, 13.21

D. 5-Methoxy-2-(tetrahydro-2H-pyran-2-yl)-3(2H)-pyridazinone (2035 g, 9.69 moles) and 2 L of methanol were added to a 22 L round bottomed flask equipped with a heating mantle, reflux condenser and mechanical stirrer. The mixture was warmed to 35° C. and 8 L of 6N HCl was added and then the mixture was heated to reflux for 2 h. The reaction mixture was then cooled slightly and transferred to a glycol cooled 22 L flask where the mixture was cooled further to 30° C. The mixture was made basic (pH 13–14) by cautious addition of 50% NaOH in small portions. The basic mixture was extracted with CH$_2$Cl$_2$ (4×3 L). The aqueous phase was then acidified with concentrated HCl (pH 1–2) to precipitate the product. The product was collected by vacuum filtration on a Buchner funnel. The product was dried to constant weight on a fluid bed dryer at 70° C. This afforded 798 g (65% yield) of 3-hydroxy-5-methoxypyridazine as a white solid which was recrystallized from methanol, mp=253° C.–255° C.

Anal. Calc. for C$_5$H$_6$N$_2$O$_2$: C, 47.62; H, 4.80;N, 22.21 Found: C, 47.60; H, 4.83;N, 22.18 E. 3-Hydroxy-5-methoxypyridazine (629.6 g, 4.99 moles) and phosphorus oxychloride (2.5 L, 27 moles) were added to a 5 L round bottomed flask equipped with a heating mantle and a mechanical stirrer. The resulting stirred slurry was rapidly heated (<30 min) to 75° C. At this temperature the heating mantle was removed. The reaction mixture continued to exotherm to a final temperature of 82.3° C. After the solids had dissolved in the darkening reaction mixture, stirring was continued an additional 2 minutes. The homogeneous reaction mixture was then rapidly cooled to room temperature with an ice/water bath. The reaction mixture was concentrated via rotary evaporator using pump vacuum and a water bath temperature of 45° C. The residue was taken up in 2 L of CH$_2$Cl$_2$ and slowly poured into a stirring mixture of 2 L CH$_2$Cl$_2$ and 6 L of H$_2$O chilled to 10° C. The layers were separated and enough 50% NaOH was added to the aqueous phase to give a pH of 2–4. The aqueous phase was extracted with additional CH$_2$Cl$_2$ (2×2 L). The combined organic layers were washed with 4 L of H$_2$O and dried (MgSO$_4$). The solution was vacuum filtered through 1 kg of silica gel. The silica gel was washed with 4 L of ethyl acetate/hexanes (1:1). The filtrate was concentrated in-vacuo to afford 564 g (78% yield) of 3-chloro-5-methoxypyridazine as a pale yellow solid. The product was stored in a freezer to minimize decomposition. The product was recrystallized from ethyl acetate/cyclohexane to give a white solid, mp=98° C.–100° C.

Anal. Calc. for C$_5$H$_5$N$_2$OCl: C, 41.54; H, 3.49;N, 19.38 Found: C, 41.62; H, 3.51;N, 19.34

EXAMPLE 2

This example describes the preparation of 3-chloro-5-(methylthio)pyridazine which is useful as an intermediate in Process III and is a specific embodiment of Process II.

3,5-Dichloropyridazine, which is known in the art, (2.0 g, 0.0135 moles) and sodium thiomethoxide (1.14 g, 0.0162 moles) were stirred in THF (50 mL) at RT under N$_2$ for 2 h. The mixture was then poured into water and extracted 2×100 mL with ethyl acetate. The organic layer was dried (MgSO$_4$), filtered and evaporated in-vacuo to give a crude solid which was recrystallized from cyclohexane/ethyl acetate to give 3-chloro-5(methylthio)pyridazine (1.64 g, 76% yield) as a brown solid, mp=98° C.–100° C.

Anal. Calc. for C$_5$H$_5$N$_2$ClS: C, 37.39; H, 3.14;N, 17.44 Found C, 37.47; H, 3.14;N, 17.49

EXAMPLE 3

This example describes the preparation of 5-methoxy-3-[3-(trifluoromethyl)phenoxy]pyridazine, Compound No. 4, and is a specific embodiment of Process III.

3-Chloro-5-methoxypyridazine (182.5 g, 1.26 moles, prepared as described above), alpha, alpha, alpha-trifluoro-m-cresol (215.0 g, 1.33 moles), CuBr (199.7 g, 1.39 moles), potassium carbonate (522 g, 3.78 moles) and 2 L of anhydrous DMSO were added to a 22 L round-bottomed flask fitted with a mechanical stirrer. The resulting heterogeneous mixture was stirred under an N$_2$ atmosphere at 90° C. for 17 h. The mixture was then partitioned between 2 L of ethyl acetate and 8 L of water. The mixture was then made acidic to pH 2 by careful addition of conc. HCl. The layers were then separated. The aqueous layer was extracted 3×1 L with ethyl acetate. The combined organic layers were washed with 0.01N HCl (2×5 L) and dried (MgSO₄). The organic layer was diluted with an equal volume of hexanes and filtered through approximately 1 kg of silica gel. The silica was washed with 4 L of 50% ethyl acetate/hexanes. The filtrate was concentrated in-vacuo to give an oily yellow solid. The crude product was taken up in 700 mL of cyclohexane. The resulting slurry was vigorously stirred for 30 min. while being chilled in an ice bath. The product was then collected by filtration and air dried for 30 min. and then dried on a fluid bed dryer at 40° C. for 20 min. to give 5-methoxy-3-3-(trifluoromethyl)phenoxy]pyridazine as an off-white solid (236.75 g, 69.5% yield), mp=89° C.–90° C.

EXAMPLE 4

This example describes the preparation of 5-(methylthio-3-[3-(trifluoromethyl)phenoxy]pyridazine, Example No. 26, which is a specific embodiment of Process III.

3-Chloro-5-(methylthio)pyridazine (500 mg, 3.11 mmoles, prepared as described above), alpha, alpha, alpha-trifluoro-m-cresol (530 mg, 3.27 mmoles), potassium carbonate (861 mg, 6.23 mmoles), CuBr (447 mg, 3.11 mmoles) and anhydrous DMSO (30 mL) were added to a round bottomed flask. The mixture was stirred under N₂ at 100° C. for 21 h and then poured into water and extracted twice with ethyl acetate. The combined organic layers were back extracted twice with water, dried (MgSO₄), filtered through silica gel and concentrated in-vacuo. The crude product was then recrystallized from cyclo-hexane to give 5-(methylthio)-3-[3-(trifluoro-methyl)phenoxy]pyridazine as an off white solid (0.45 g, 50% yield), mp=80° C.–81° C.

Several other compounds of the present invention were prepared using generally the procedures illustrated above or other procedure obvious to one skilled in the art. Specific compounds illustrated of the present invention are given below where the prepared compounds are structurally depicted and named. Melting points and elemental analyses are provided for these compounds in the following table.

| COMPOUND NO. | Name | Structure | Analysis (%) Calc'd | Found |
|---|---|---|---|---|
| 1 | PYRIDAZINE, 4-CHLORO-5-METHOXY-3-[3-(TRIFLUOROMETHYL)-PHENOXY]- MP: 110.0–111.0 | 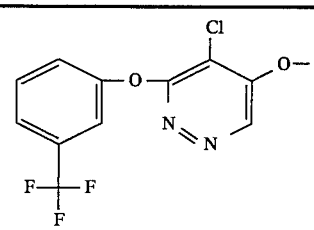 | C 47.31<br>H 2.65<br>N 9.20 | 47.39<br>2.66<br>9.12 |
| 2 | PYRIDAZINE, 3-(4-CHLORO-3,5-DIMETHYLPHENOXY)-5-METHOXY- MP: 131.0–132.0 | 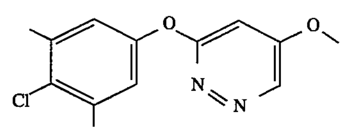 | C 58.99<br>Cl 13.39<br>H 4.95<br>N 10.58 | 59.01<br>13.40<br>4.97<br>10.54 |
| 3 | PYRIDAZINE, 3-CHLORO-6-[3-(TRIFLUOROMETHYL)PHENOXY]- MP: 69.0–71.0 | 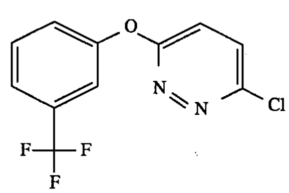 | C 48.11<br>H 2.20<br>N 10.20 | 48.21<br>2.20<br>10.19 |
| 4 | PYRIDAZINE, 5-METHOXY-3-[3-(TRIFLUOROMETHYL)PHENOXY]- MP: 89.0–90.0 | 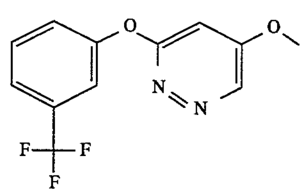 | C 53.34<br>H 3.36<br>N 10.37 | 50.40<br>3.13<br>9.75 |
| 5 | PYRIDAZINE, 5-METHOXY-3,4-BIS[3-(TRIFLUOROMETHYL)-PHENOXY]- MP: 79.0–80.0 | 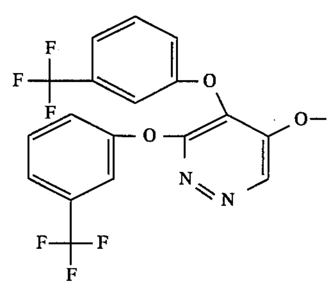 | C 53.03<br>H 2.81<br>N 6.51 | 52.56<br>2.77<br>6.46 |

-continued

| COMPOUND NO. | Name | Structure | Analysis (%) Calc'd | Found |
|---|---|---|---|---|
| 6 | PYRIDAZINE, 4-CHLORO-3-(3-CHLOROPHENOXY)-5-METHOXY- MP: 134.0–135.0 | 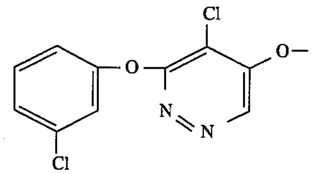 | C 48.73<br>H 2.97<br>N 10.33 | 48.53<br>2.97<br>10.24 |
| 7 | PYRIDAZINE, 5-METHOXY-3-PHENOXY- MP: 109.0–110.0 | 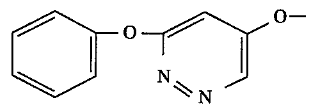 | C 65.34<br>H 4.98<br>N 13.85 | 64.76<br>4.89<br>13.77 |
| 8 | PYRIDAZINE, 3-(3-CHLORO-PHENOXY)-5-METHOXY- MP: 56.0 | 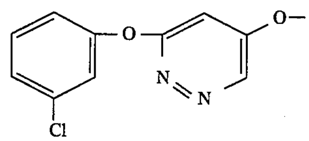 | C 55.83<br>H 3.83<br>N 11.84 | 55.74<br>3.85<br>11.75 |
| 9 | PYRIDAZINE, 3-[3,5-BIS(TRI-FLUOROMETHYL)PHENOXY]-4-CHLORO-5-METHOXY- MP: 176.0–178.0 | 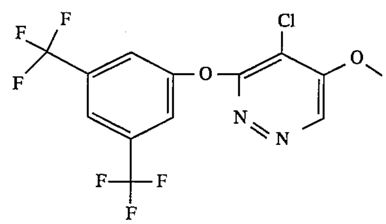 | C 41.90<br>H 1.89<br>N 7.52 | 42.06<br>1.84<br>7.41 |
| 10 | PYRIDAZINE, 5-ETHOXY-3-[3-(TRI-FLUOROMETHYL)PHENOXY]- MP: 124.0–125.0 | 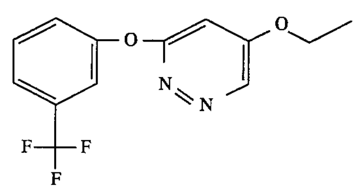 | C 54.93<br>H 3.90<br>N 9.86 | 55.00<br>3.92<br>9.85 |
| 11 | PYRIDAZINE, 3-[3,5-BIS(TRI-FLUOROMETHYL)PHENOXY]-5-METHOXY- MP: 125.0–127.0 | 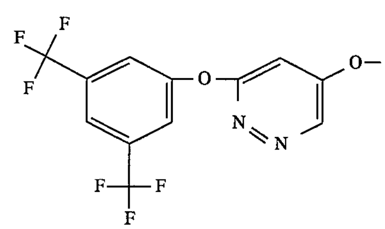 | C 46.17<br>H 2.38<br>N 8.28 | 46.32<br>2.41<br>8.24 |
| 12 | PYRIDAZINE, 3-(3-FLUORO-PHENOXY)-5-METHOXY- MP: 91.0–92.0 | 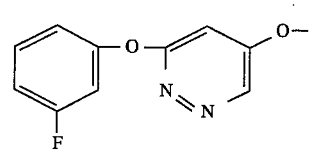 | C 60.00<br>H 4.12<br>N 12.72 | 60.03<br>4.19<br>12.76 |
| 13 | PYRIDAZINE, 3-(3-METHOXY-PHENOXY)-5-METHOXY- MP: 66.0–67.5 | 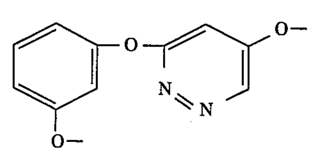 | C 62.06<br>H 5.21<br>N 12.06 | 62.03<br>5.25<br>12.08 |
| 14 | PYRIDAZINE, 5-METHOXY-3-(3-NITROPHENOXY)- MP: 121.0–124.0 | 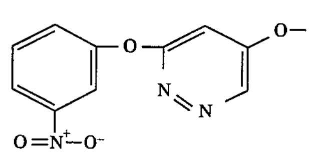 | C 52.49<br>H 3.80<br>N 16.69 | 52.45<br>3.65<br>16.69 |

-continued

| COMPOUND NO. | Name | Structure | Analysis (%) Calc'd | Found |
|---|---|---|---|---|
| 15 | PYRIDAZINE, 5-METHOXY-3-(4-METHOXYPHENOXY)- MP: 125.0–126.0 | 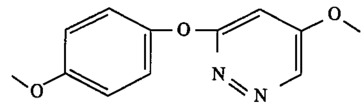 | C 62.06<br>H 5.21<br>N 12.06 | 61.95<br>5.21<br>12.00 |
| 16 | PYRIDAZINE, 5-METHOXY-3-[4-(TRIFLUOROMETHYL)PHENOXY]- MP: 126.0–127.0 | 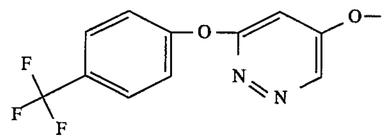 | C 53.34<br>H 3.36<br>N 10.37 | 53.48<br>3.39<br>10.33 |
| 17 | PYRIDAZINE, 5-METHOXY-3-[2-(TRIFLUOROMETHYL)PHENOXY]- | 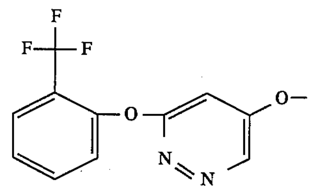 | C 53.34<br>H 3.36<br>N 10.37 | 53.06<br>3.37<br>10.15 |
| 18 | PYRIDAZINE, 3-(2,4-DICHLOROPHENOXY)-5-METHOXY- MP: 131.0–132.0 | 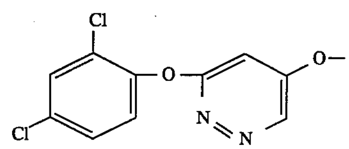 | C 48.73<br>H 2.97<br>N 10.33 | 48.79<br>2.92<br>10.35 |
| 19 | PYRIDAZINE, 3-(4-FLUOROPHENOXY)-5-METHOXY- MP: 138.0–139.0 | 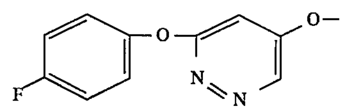 | C 60.00<br>H 4.12<br>N 12.72 | 59.65<br>4.08<br>12.61 |
| 20 | PYRIDAZINE, 5-METHOXY-3-(2-METHOXYPHENOXY)- MP: 115.0–116.0 | 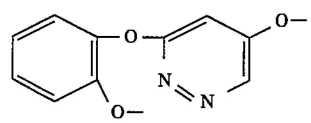 | C 60.88<br>H 5.32<br>N 11.83 | 60.50<br>5.03<br>11.76 |
| 21 | PYRIDAZINE, 3-(2-FLUOROPHENOXY)-5-METHOXY- MP: 52.0–54.0 | 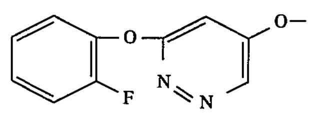 | C 60.00<br>H 4.12<br>N 12.72 | 59.95<br>4.12<br>12.67 |
| 22 | PYRIDAZINE, 5-METHXOY-3-(2,4-DINITROPHENOXY)- MP: 149.0–151.0 | 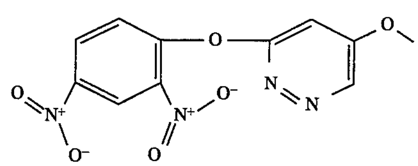 | C 45.21<br>H 2.76<br>N 19.17 | 45.50<br>2.71<br>19.45 |
| 23 | BENZOIC ACID, 2-[(5-METHOXY-3-PYRIDAZINYL)OXY]-, METHYL ESTER MP: 101.0–103.0 | 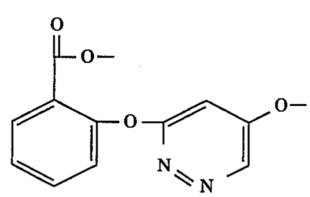 | C 60.00<br>H 4.65<br>N 10.76 | 59.84<br>4.66<br>10.71 |
| 24 | PYRIDAZINE, 5-METHYL-3-[3-(TRIFLUOROMETHYL)PHENOXY]- | 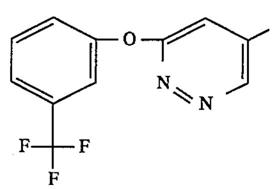 | C 56.70<br>H 3.57<br>N 11.02 | 57.16<br>3.75<br>10.39 |

-continued

| COMPOUND | | | | Analysis (%) | |
|---|---|---|---|---|---|
| NO. | Name | Structure | | Calc'd | Found |
| 25 | PYRIDAZINE, 4-METHYL-3-[3-(TRIFLUOROMETHYL)PHEN-OXY]- MP: 64.0–65.0 | | C<br>H<br>N | 56.70<br>3.57<br>11.02 | 56.95<br>3.60<br>11.12 |
| 26 | PYRIDAZINE, 5-(METHYLTHIO)-3-[3-(TRIFLUOROMETHYL)-PHENOXY]- MP: 80.0–81.0 | | C<br>H<br>N | 50.35<br>3.17<br>9.79 | 50.42<br>3.19<br>9.81 |
| 27 | 4-PYRIDAZINAMINE, N-METHYL-6-[3-(TRIFLUOROMETHYL)-PHENOXY]- MP: 116.0–117.0 | | C<br>H<br>N | 53.54<br>3.74<br>15.61 | 53.60<br>3.77<br>15.62 |
| 28 | PYRIDAZINE, 3,5-BIS[3-(TRI-FLUOROMETHYL)PHENOXY]- MP: 107.0–108.0 | | C<br>H<br>N | 54.01<br>2.52<br>7.00 | 54.08<br>2.55<br>6.98 |
| 29 | 5-PYRIDAZINOL, 3-[3-(TRI-FLUOROMETHYL)PHENOXY]- | | C<br>H<br>N | 51.57<br>2.75<br>10.93 | 49.83<br>2.81<br>10.49 |
| 30 | PYRIDAZINE, 5-(DIFLUORO-METHOXY)-3-[3-(TRIFLUORO-METHYL)PHENOXY]- | | C<br>H<br>N | 47.07<br>2.30<br>9.15 | 46.99<br>2.31<br>9.12 |
| 31 | PYRIDAZINE, 3-(1-NAPHTHA-LENYLOXY)-5-METHOXY- MP: 135.8–138.3 | | C<br>H<br>N | 71.42<br>4.79<br>11.10 | 71.41<br>4.81<br>11.14 |
| 32 | PYRIDAZINE, 3-(2-NAPHTHA-LENYLOXY)-5-METHOXY- MP: 128.8–130.8 | | C<br>H<br>N | 71.42<br>4.79<br>11.10 | 71.38<br>4.81<br>11.09 |

-continued

| COMPOUND NO. | Name | Structure | Analysis (%) Calc'd | Found |
|---|---|---|---|---|
| 33 | PYRIDAZINE, 5-METHOXY-3-[3-TRIFLUOROMETHOXY)PHENOXY]- MP: 109.0–111.0 | 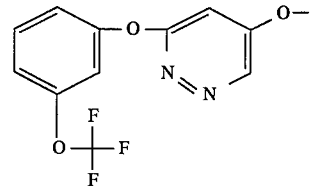 | C 50.36<br>H 3.17<br>N 9.79 | 50.44<br>3.20<br>9.83 |
| 34 | PYRIDAZINE, 5-METHOXY-3-[2-METHYL-5-(TRIFLUOROMETHYL)PHENOXY]- MP: 111.0–113.0 | 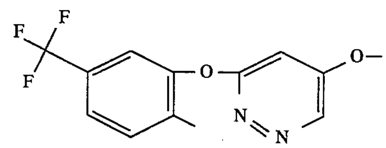 | C 54.93<br>H 3.90 | 55.06<br>3.90 |
| 35 | PYRIDAZINE, 5-METHOXY-3-[3-(TRIMETHYLSILYL)PHENOXY]- MP: 79.0–80.0 | 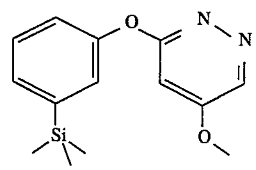 | C 61.28<br>H 6.61 | 61.41<br>6.58 |
| 36 | PYRIDAZINE, 3-[3-(1,1-DIMETHYLETHYL)PHENOXY]-5-METHOXY- MP: 80.0–82.0 | 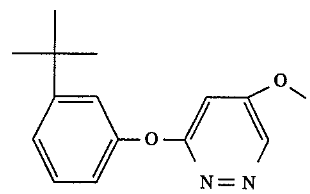 | C 69.74<br>H 7.02 | 69.66<br>6.99 |
| 37 | PYRIDAZINE, 3-[3-(DIFLUOROMETHOXY)PHENOXY]-5-METHOXY- MP: 66.0–68.0 | 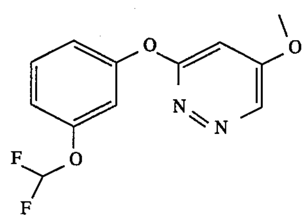 | C 53.74<br>H 3.76 | 53.81<br>3.76 |
| 38 | PYRIDAZINE, 5-METHOXY-3-[3-(TRIFLUOROMETHYL)PHENOXY]-, 1-OXIDE MP: 159.4–160.0 | 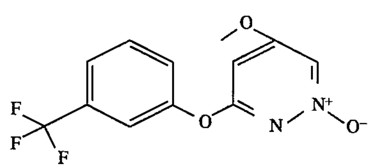 | C 50.36<br>H 3.17<br>N 9.79 | 50.27<br>3.16<br>9.78 |
| 39 | PYRIDAZINE, 5-METHYL-3-PHENOXY-, 1-OXIDE MP: 73.0–75.0 | 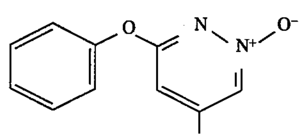 | C 65.34<br>H 4.98<br>N 13.85 | 65.28<br>4.97<br>13.82 |
| 40 | PYRIDAZINE, 3-CHLORO-4-METHYL-6-PHENOXY- MP: 141.0–143.0 | 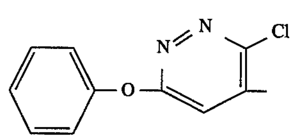 | C 59.88<br>H 4.11<br>N 12.70 | 60.08<br>4.14<br>12.60 |

| COMPOUND | | | Analysis (%) | |
|---|---|---|---|---|
| NO. | Name | Structure | Calc'd | Found |
| 41 | PYRIDAZINE, 5-METHOXY-3-[3-(TRIETHYLSILYL)PHENOXY]- MP: 87.0–88.5 | | C 64.52<br>H 7.64<br>N 8.85 | 64.53<br>7.63<br>8.87 |
| 42 | PYRIDAZINE, 5-(PHENYLTHIO)-3-[3-(TRIFLUOROMETHYL)-PHENOXY]- | | | |
| 43 | PYRIDAZINE, 3-BROMO-4-METHYL-6-PHENOXY- MP: 130.0–133.0 | | C 49.84<br>H 3.42<br>N 10.57 | 49.66<br>3.44<br>10.50 |
| 44 | PYRIDAZINE, 3-ETHYL-4-METHYL-6-PHENOXY- | | C 72.87<br>H 6.59<br>N 13.07 | 72.94<br>6.59<br>13.05 |
| 45 | PYRIDAZINE, 3-METHOXY-4-METHYL-6-PHENOXY- MP: 86.0–88.0 | | C 66.65<br>H 5.59<br>N 12.95 | 66.46<br>5.63<br>12.87 |

PRE-EMERGENT ACTIVITY ON PLANTS

As noted above, compounds of this invention have been found to be effective as herbicides, particularly as pre-emergent herbicides. Table A summarizes results of tests conducted to determine the pre-emergent herbicidal activity of the compounds of this invention. The herbicidal ratings used in Table A were assigned according to a scale based on the percent inhibition of each plant species. The symbol C represents complete control and N or a hyphen represents no data.

One set of pre-emergent tests was conducted as follows:

Topsoil was placed in a pan and compacted to a depth of 0.95 to 1.27 cm from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha) or other rate as indicated in Table A. After treatment, the pans were moved to a greenhouse bench where they were watered as needed to give adequate moisture for germination and growth.

Approximately 10–14 days (usually 11 days) after planting and treating, the plants were observed and the results recorded.

The plant species usually regarded as weeds which were utilized in one set of pre-emergent activity tests, the data for which are shown in Table A, are identified by letter headings printed above the columns according to the following legend:

COBU—Cocklebur
VELE—Velvetleaf
DOBR—Downy Brome
MOGL—Morning Glory
BYGR—Barnyardgrass
ANBG—Annual Bluegrass
SEJG—Seedling Johnsongrass
YENS—Yellow Nutsedge *
INMU—Indian Mustard
WIBW—Wild Buckwheat
SOYB—Soybean
COTT—Cotton
RAPE—Rape
HEMP—Hemp Sesbania
CHWD—Chickenweed, Common WHEA—Wheat
SORG—Sorghum (Grain)
CORN—Corn
PROSO—Proso Millet
CRAB—Crabgrass, Large
FOXT—Foxtail, Green
RICE—Rice
JOHN—Johnsongrass, Rhizome
CANA—Canada Thistle
FDBW—Field Bindweed
QUACK—Quackgrass, Rhizome

*Grown from vegetative propagules

TABLE A

| CP NO. | Rate Kg/Ha | SOYB | COTT | RAPE | COBU | WIBW | MOGL | HEMP | CHWD | VELE |
|---|---|---|---|---|---|---|---|---|---|---|
| 1 | 11.2 | 0 | 5 | 0 | 0 | 10 | 5 | 0 | 5 | 0 |
| 2 | 5.6 | 50 | 50 | 100 | 35 | 100 | 95 | 100 | 90 | 100 |

| CP NO. | Rate Kg/Ha | WHEA | SORG | CORN | DOBR | PROSO | BYGR | CRAB | FOXT | RICE |
|---|---|---|---|---|---|---|---|---|---|---|
| 1 | 11.2 | 0 | 0 | 0 | 0 | 10 | 0 | 90 | 0 | 25 |
| 2 | 5.6 | 70 | 65 | 90 | 100 | 90 | 100 | 100 | 100 | 35 |

| CP No. | Rate Kg/Ha | CRAB | SEJG | RICE | SOYB | CORN | BYGR | COTT | VELE | MOGL | COBU |
|---|---|---|---|---|---|---|---|---|---|---|---|
| 3 | 5.6 | 100 | 90 | 35 | 50 | 40 | 100 | 5 | 95 | 95 | 0 |
| 6 | 11.1 | 65 | 30 | 0 | 0 | 0 | 10 | 0 | 0 | 0 | 0 |
| 7 | 5.6 | 100 | 98 | 60 | 40 | 35 | 100 | 20 | 75 | 70 | 25 |
| 10 | 2.6 | 100 | 99 | 50 | 50 | 30 | 99 | 50 | 100 | 50 | 25 |
| 12 | 5.6 | 99 | 100 | 65 | 98 | 95 | 100 | 98 | 100 | 100 | 30 |
| 13 | 5.6 | 50 | 50 | 0 | 10 | 0 | 60 | 0 | 99 | 25 | 0 |
| 14 | 5.6 | 100 | 100 | 60 | 75 | 5 | 75 | 100 | 100 | 35 | 100 |
| 16 | 5.6 | 100 | 100 | 25 | 50 | 50 | 99 | 5 | 100 | 90 | 0 |
| 18 | 11.1 | 100 | 99 | 10 | 5 | 0 | 98 | 5 | 75 | 70 | 0 |
| 25 | 5.6 | 100 | 99 | 50 | 25 | 5 | 100 | 5 | 75 | 60 | 25 |
| 27 | 5.6 | 99 | 99 | 25 | 0 | 0 | — | — | — | — | — |
| 30 | 5.6 | 100 | 99 | 80 | 70 | 10 | 100 | 75 | 100 | 100 | 100 |
| 32 | 11.1 | 100 | 90 | 25 | 20 | 15 | 75 | 10 | 65 | 35 | 30 |
| 34 | 1.12 | 99 | 80 | 60 | 40 | 0 | 99 | 50 | 100 | 70 | 30 |
| 36 | 1.12 | 50 | 85 | 5 | — | — | — | — | — | — | — |

| CP No. | Rate Kg/Ha | YENS | ANBG | SEJG | DOBR | MOGL | COBU | VELE | INMU | WIBW | BYGR |
|---|---|---|---|---|---|---|---|---|---|---|---|
| 3 | 11.1 | 30 | 50 | 90 | 20 | 30 | 10 | 30 | 80 | 50 | 100 |
| 5 | 11.1 | 0 | 20 | 50 | 0 | 50 | 0 | 30 | 40 | 20 | 10 |
| 6 | 11.1 | 0 | 20 | 20 | 0 | 20 | 0 | 0 | 80 | 0 | 0 |
| 9 | 11.1 | 0 | 0 | 0 | 0 | 0 | 0 | 0 | 0 | — | 0 |
| 10 | 11.1 | 60 | 90 | 80 | 30 | 50 | 20 | 90 | 100 | 100 | 100 |
| 11 | 11.1 | 0 | 10 | 0 | 0 | 20 | 10 | 10 | 20 | 10 | 10 |
| 12 | 11.1 | 50 | 100 | 100 | 30 | 70 | 20 | 100 | 100 | 90 | 100 |
| 13 | 11.1 | 30 | 80 | 80 | 20 | 60 | 10 | 30 | 90 | 70 | 50 |
| 15 | 11.1 | 20 | 20 | 20 | 0 | 0 | 0 | 20 | 50 | 30 | 0 |
| 16 | 11.1 | 50 | 100 | 100 | 60 | 80 | 10 | 100 | 100 | 100 | 100 |
| 17 | 5.6 | 20 | 90 | 80 | 10 | 60 | 10 | 80 | 90 | 80 | 90 |
| 18 | 11.1 | 20 | 60 | 40 | 20 | 40 | 20 | 20 | 90 | 60 | 70 |
| 19 | 11.1 | 50 | 100 | 90 | 20 | 60 | 10 | 70 | 80 | 70 | 100 |
| 20 | 11.1 | 0 | 0 | 0 | 0 | 0 | 0 | 0 | 20 | 0 | 0 |
| 21 | 11.1 | 20 | 80 | 60 | 20 | 20 | 0 | 30 | 70 | 40 | 50 |
| 22 | 11.1 | 0 | 0 | 0 | 0 | 0 | 0 | 0 | 0 | 0 | 0 |

| CP No. | Rate Kg/Ha | YENS | ANBG | SEJG | DOBR | MOGL | COBU | VELE | INMU | WIBW | BYGR |
|---|---|---|---|---|---|---|---|---|---|---|---|
| 23 | 11.1 | 0 | 0 | 10 | 20 | 0 | 10 | 10 | 20 | 10 | 10 |
| 26 | 11.1 | 50 | 80 | 20 | 40 | 80 | 20 | 20 | 90 | 50 | 90 |
| 27 | 11.1 | 40 | 50 | 40 | 40 | 60 | 40 | 90 | 100 | 80 | 70 |
| 28 | 11.1 | 0 | 0 | 0 | 0 | 0 | 0 | 0 | 0 | 0 | 0 |
| 29 | 11.1 | 0 | 0 | 0 | 0 | 0 | 0 | 0 | 30 | — | 0 |

TABLE A-continued

| CP No. | Rate Kg/Ha | COTT | RICE | SOYB | CORN | WHEA | JOHN | YENS | CANA | FDBW | QUAC |
|---|---|---|---|---|---|---|---|---|---|---|---|
| 30 | 11.1 | 0 | 0 | 0 | 0 | 10 | 10 | 30 | 40 | 90 | 0 |
| 31 | 11.1 | 20 | 0 | 0 | 0 | 0 | 20 | 0 | 20 | 0 | 0 |
| 32 | 11.1 | 30 | 50 | 20 | 30 | 50 | 70 | 70 | 70 | 20 | 50 |
| 33 | 1.12 | 70 | 100 | 100 | 100 | 80 | 30 | 100 | 100 | 90 | 100 |
| 34 | 11.1 | 90 | 90 | 90 | 90 | 90 | 60 | 90 | 90 | 90 | 90 |
| 35 | 11.1 | 10 | 90 | 30 | 20 | 90 | 10 | 100 | 100 | 40 | 80 |
| 36 | 11.1 | 70 | 100 | 100 | 10 | 100 | 10 | 100 | 100 | 70 | 90 |
| 37 | 1.12 | 30 | 90 | 80 | 30 | 100 | 0 | 90 | 100 | 60 | 90 |
| 38 | 1.12 | — | 70 | — | 30 | — | — | 100 | 100 | — | — |
| 39 | 1.12 | 0 | 0 | 0 | 0 | 10 | 0 | 0 | 0 | 0 | 0 |
| 40 | 1.12 | 20 | 100 | 90 | 90 | 10 | 0 | 0 | 0 | 0 | 100 |

| CP No. | Rate Kg/Ha | COTT | RICE | SOYB | CORN | WHEA | JOHN | YENS | CANA | FDBW | QUAC |
|---|---|---|---|---|---|---|---|---|---|---|---|
| 4 | 5.6 | 90 | 99 | 99 | 75 | 100 | 20 | 60 | 65 | 99 | 95 |
| 8 | 5.6 | 35 | 80 | 75 | 65 | 90 | 15 | 65 | 100 | 90 | 90 |
| 24 | 5.6 | 40 | 90 | 98 | 95 | 99 | 20 | 80 | 100 | 99 | 95 |

| CP No. | Rate Kg/Ha | FOXT | YENS | BYGR | RICE | CORN | VELE | MOGL | COBU | SOYB |
|---|---|---|---|---|---|---|---|---|---|---|
| 41 | 5.0 | 35 | 0 | 95 | 0 | 0 | 35 | 0 | 0 | 0 |
| 42 | 5.0 | 0 | 0 | 0 | 0 | 0 | 0 | 0 | 0 | 0 |
| 43 | 1.0 | 85 | 30 | 100 | 85 | 0 | 0 | 10 | 25 | 0 |
| 44 | 1.0 | 100 | 45 | 90 | 35 | 25 | 35 | 40 | 35 | 10 |
| 45 | 1.0 | 50 | 10 | 20 | 25 | 0 | 45 | 50 | 0 | 10 |

POST-EMERGENT HERBICIDE ACTIVITY ON PLANTS

Although, as has been stated above, the compounds of this invention exhibit predominantly preemergence activity in greenhouse testing, nevertheless many of these compounds are active post-emergent herbicides. The post-emergent activity is best seen on younger plants treated at the 1–½ to 2 leaf stage. In the tests which follow, larger and more developed plants were used.

The post-emergence herbicidal activity of compounds of this invention was demonstrated by greenhouse testing, and the results are shown in the following Table B.

Top soil was placed in pans having holes in the bottom and compacted to a depth of 0.95 to 1.27 cm from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.21 kg/ha or other rate as indicated in Table B while applying a total amount of solution or suspension equivalent to 1870 L/ha. The pans were returned to the greenhouse and watered as before and the injury to the plants as compared to those in control pans was observed at approximately 10–14 days (usually 11 days). The plant identifying codes and symbols in Table B are the same as above defined.

TABLE B

| CP No. | Rate Kg/Ha | YENS | ANBG | SEJG | DOBR | BYGR | MOGL | COBU | VELE | INMU | WIBW |
|---|---|---|---|---|---|---|---|---|---|---|---|
| 1 | 11.1 | 0 | 0 | 10 | 0 | 0 | 10 | 10 | 0 | 20 | 10 |
| 3 | 11.1 | 0 | 10 | 10 | — | — | — | — | — | — | — |
| 5 | 11.1 | 0 | 20 | 10 | 0 | 10 | 20 | 30 | 40 | 50 | 30 |
| 6 | 11.1 | 0 | 0 | 0 | 0 | 0 | 0 | 20 | 10 | — | 30 |
| 8 | 11.1 | 20 | 30 | 50 | 20 | 20 | 50 | 80 | 30 | 60 | 80 |
| 9 | 11.1 | 0 | 0 | 0 | 0 | 0 | 0 | 0 | 0 | 0 | 0 |
| 10 | 11.1 | 0 | 30 | 10 | 0 | 10 | 10 | 20 | 20 | 30 | 20 |
| 11 | 11.1 | 0 | 20 | 60 | 20 | 50 | 20 | 30 | 40 | 60 | 10 |
| 12 | 11.1 | 10 | 40 | 40 | 0 | 20 | 30 | 30 | 30 | 40 | 99 |
| 13 | 11.1 | 10 | 10 | 20 | 0 | 10 | 20 | 20 | 10 | 20 | 40 |
| 14 | 11.1 | 10 | 10 | 0 | 0 | 20 | 30 | 20 | 10 | 20 | 40 |
| 15 | 11.1 | 0 | 0 | 0 | 10 | 0 | 20 | 20 | 20 | 20 | 30 |
| 16 | 11.1 | 10 | 20 | 40 | 10 | 20 | 20 | 10 | 10 | 40 | 50 |
| 17 | 11.1 | 0 | 10 | 20 | 0 | 10 | 10 | 20 | 10 | 20 | 40 |
| 18 | 11.1 | 0 | 0 | 0 | 0 | 10 | 0 | 0 | 0 | 20 | 10 |
| 19 | 11.1 | 0 | 10 | 10 | 10 | 20 | 10 | 10 | 20 | 30 | 40 |
| 20 | 11.1 | 0 | 0 | 0 | 10 | 10 | 0 | 0 | 20 | 10 | 10 |
| 21 | 11.1 | 0 | 10 | 20 | 20 | 10 | 10 | 10 | 20 | 20 | 40 |
| 22 | 11.1 | 0 | 0 | 0 | 0 | 0 | 0 | 10 | 10 | 0 | 0 |
| 23 | 11.1 | 0 | 0 | 10 | 20 | 10 | 0 | 10 | 10 | 20 | 10 |

| CP No. | Rate Kg/Ha | YENS | ANBG | SEJG | DOBR | BYGR | MOGL | COBU | VELE | INMU | WIBW |
|---|---|---|---|---|---|---|---|---|---|---|---|
| 24 | 11.1 | 10 | 40 | 60 | 30 | 60 | 20 | 50 | 10 | 40 | 60 |
| 25 | 11.1 | 0 | 10 | 30 | 30 | 0 | 10 | 10 | 20 | 30 | 20 |
| 26 | 11.1 | 0 | 90 | 20 | 50 | 70 | 30 | 50 | 30 | 80 | 90 |
| 27 | 11.1 | 10 | 10 | 10 | 10 | 90 | 20 | 40 | 30 | 30 | 50 |
| 28 | 11.1 | 0 | 0 | 0 | 10 | 0 | 10 | 10 | 0 | 30 | 20 |
| 29 | 11.1 | 0 | 0 | 0 | 0 | 0 | 0 | 0 | 0 | 30 | 90 |
| 30 | 11.1 | 0 | 0 | 0 | 0 | 0 | 10 | 10 | 30 | 40 | 90 |
| 31 | 11.1 | 0 | 0 | 0 | 0 | 0 | 0 | 0 | 20 | 20 | 0 |
| 32 | 11.1 | 0 | 0 | 0 | 0 | 0 | 0 | 0 | 20 | 20 | 20 |

TABLE B-continued

| | | | | | | | | | | |
|---|---|---|---|---|---|---|---|---|---|---|
| 33 | 1.12 | 10 | 50 | 50 | 0 | 50 | 40 | 80 | 60 | 60 | 80 |
| 34 | 11.1 | 30 | 100 | 80 | — | — | — | — | — | — | — |
| 35 | 11.1 | 10 | 60 | 30 | 20 | 50 | 70 | 30 | 60 | 70 | 10 |
| 36 | 11.1 | 20 | 50 | 50 | 20 | 40 | 60 | 50 | 60 | 70 | 80 |
| 37 | 1.12 | 0 | 0 | 0 | 0 | 0 | 60 | 20 | 10 | 60 | 10 |
| 38 | 1.12 | — | — | 0 | 0 | — | — | 10 | 40 | — | — |
| 39 | 1.12 | 0 | 0 | 0 | 0 | 0 | 0 | 0 | 0 | 0 | 0 |
| 40 | 1.12 | 0 | 0 | 0 | 0 | 0 | 30 | 0 | 0 | 0 | 0 |

| CP No. | Rate Kg/Ha | SOYB | COTT | RAPE | COBU | WIBW | MOGL | HEMP | CHWD | VELE |
|---|---|---|---|---|---|---|---|---|---|---|
| 2 | 5.6 | 25 | 65 | 30 | 40 | 100 | 50 | 99 | 60 | 100 |

| CP No. | Rate Kg/Ha | WHEA | RICE | SORG | CORN | DOBR | PROSO | BYGR | CRAB | FOXT |
|---|---|---|---|---|---|---|---|---|---|---|
| 2 | 5.6 | 20 | 35 | 35 | 50 | 30 | 50 | 60 | 90 | 85 |

| CP No. | Rate Kg/Ha | CRAB | SEJG | RICE | SOYB | CORN | BYGR | COTT | VELE | MOGL | COBU |
|---|---|---|---|---|---|---|---|---|---|---|---|
| 7 | 11.1 | 40 | 5 | 5 | 60 | 0 | 5 | 70 | 25 | 50 | 25 |
| 34 | 5.6 | 90 | 20 | 5 | 90 | 20 | 20 | 25 | 60 | 50 | 60 |

| CP No. | Rate Kg/Ha | FOXT | YENS | BYGR | RICE | CORN | VELE | MOGL | COBU | SOYB |
|---|---|---|---|---|---|---|---|---|---|---|
| 41 | 5.0 | 20 | 15 | 15 | 5 | 5 | 25 | 20 | 25 | 20 |
| 42 | 5.0 | 0 | 0 | 5 | 0 | 0 | 0 | 0 | 0 | 0 |
| 43 | 1.0 | 0 | 0 | 0 | 0 | 10 | 40 | 10 | 10 | 20 |
| 44 | 1.0 | 0 | 0 | 0 | 0 | 0 | 50 | 10 | 0 | 20 |
| 45 | 1.0 | 0 | 0 | 0 | 0 | 0 | 70 | 40 | 20 | 25 |

| CP No. | Rate Kg/Ha | COTT | RICE | SOYB | CORN | WHEA | JOHN |
|---|---|---|---|---|---|---|---|
| 4 | 5.6 | 90 | 99 | 99 | 75 | 100 | 20 |

As can be seen from the data above, some of the compounds are suitably safe on certain crops and can thus be used for selective control of weeds in these crops. Known safeners can be added to the formulated herbicidal formulation when additional crop safening is indicated.

The methods of making such compositions are well known. Solutions are prepared by simply mixing the ingredients to be included therein. Fine solid compositions are made by blending and, usually, grinding as in a hammer or fluid energy mill. Suspensions are prepared by wet milling, for example. Granules and pellets can be made by spraying the material containing the active material upon preformed granular carriers or by agglomeration techniques or the like.

The herbicidal compositions 6f this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the monohigher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or antifoaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsions of very finely-divided particles. The resulting concentrated aqueous suspension is characterized by its extremely small particle size, so that when diluted and sprayed, coverage is very uniform. Suitable concentrations of these formulations contain from about 0.1–60%, preferably 5–50% by weight of active ingredient, the upper limit to be determined by the solubility limit of active ingredient in the solvent.

Concentrates are usually solutions of active ingredient in water-immiscible or partially water-immiscible solvents together with a surface active agent. Suitable solvents for the active ingredient of this invention include N,N-dimethylformamide, dimethylsulfoxide, N-methyl-pyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite clay or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1, 2,4-triazole
6,7-Dihydrodipyrido (1,2-d:a', 1'-c)-pyrazidiinium salt
5-Bromo-3-isopropyl-6-methyluracil 1,1'-dimethyl-4,4'-bipyridinium
2-(4-Isopropyl-4-methyl-5-oxo-2-imidazolin-2-yl(-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-n'-(3-chloro-4 -methylphenyl) urea
3 -(3,4-Dichlorophenyl )-1,1-dimethylurea
1,3-Dimethyl-3-(2-benzothiazolyl ) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl)aminocarbonyl]-benzenesulfonamide
Methyl-2-(((((4,6-dimethyl-2-pyrimidinyl)amino)carbonyl)amino)sulfonyl)benzoate
Ethyl 2-[methyl 2-(((((4,6-dimethyl-2-pyrimidinyl)amino)carbonyl) amino) sulfonyl )] benzoate
Methyl-2 ((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate Carbamates/Thiolcarbamates 2-Chloroallyl diethyldithiocarbamate
S-(4-Chlorobenzyl)N,N-diethylthiolcarbamate
Isopropyl N-(3-chlorophenyl) carbamate
S-2,3-Dichloroallyl N,N-diisopropylthiolcarbamate
S-N,N-dipropylthiolcarbamate
S-Propyl N,N-dipropylthiolcarbamate
S-2,3,3-Trichloroallyl N,N-diisopropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl]amino]phenyl)acetamide N-isopropyl-2-chloroacetanilide
2',6'-Diethyl-N-methoxymethyl-2-chloroacetanilide
2'-Methyl-6'-ethyl-N-(2-methoxypropyl-2-yl)-2chloroacetanilide
α,α,α-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2-Dichlorophenoxyacetic acid
Methyl-2-[4-(2,4-dichlorophenoxy)phenoxy]propionate
3-Amino-2,5-dichblorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts
Butyl 2-[4-[[5-(trifluoromethyl)-2-pyridinyl]oxy]phenoxy] propanoate Ethers 2,4-Dichlorophenyl-4-nitrophenyl ether
2-Chloro-α,α,α-trifluoro-p-tolyl-3-ethoxy-4-nitrodiphenyl ether
5-(2-Chloro-4-trifluoromethylphenoxy)-N-methyl sulfonyl-2-nitrobenzamide
1'-(Carboethoxy) ethyl 5-[2-chloro-4-(trifluoromethyl)phenoxy]-2-nitrobenzoate Miscellaneous 2,6-Dichlorobenzonitrile
Monosodium acid methanearsonate
Disodium methanearsonate
2-(2-Chlorophenyl)methyl-4,4-dimethyl-3-isoxazolidinone
7-Oxabicyclo (2.2.1) heptane, 1-methyl-4-(1-methyl-ethyl-2-(2-methylphenylmethoxy)-, exo Fertilizers useful in combination with the active ingredients include, for example, ammonium nitrate, urea, potash and superphosphate. Other useful additaments include materials in which plant organisms take root and grow such as compost, manure, humus, sand and the like.

It is common practice to use various antidotal or safening compounds to reduce the phytotoxicity of certain herbicides to various crops, especially corn. Accordingly, together with the 3-pyrazolyl-oxypyridazines of the present invention, alone or in combination with a herbicidal 2-chloroacetanilide, one can include in the formulations a safening amount of a suitable antidotal compound. Among suitable safeners for inclusion in the formulations of the present invention are fluorazole, cyometrinal, oxabetrinil, dichlormid, AD-67, 1,3-oxazolidine dichloroacetamides and other compounds known in the art as antidotes for herbicides, especially for corn. One preferred safener is 3-(dichloroacetyl)-5-(2-furanyl)-2,2-dimethyl oxazolidine.

Herbicidal formulations of the types described above are exemplified in several illustrative embodiments below.

| | | Weight Percent |
|---|---|---|
| I. Emulsifiable Concentrates | | |
| A. | Compound of Example No. 13 | 11.0 |
| | Free acid of complex organic phosphate or aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 23 | 25.00 |
| | Free acid of complex organic phosphate or aromatic or aliphatic hydrophobe base (e.g., GAFAC RE-610) | 5.00 |
| | Polyoxyethylene/polyoxyproplene block copolymer with butanol (e.g., Tergitol XH) | 1.60 |
| | Phenol | 4.75 |
| | Monochlorobenzene | 63.65 |
| | | 100.00 |
| II. Flowables | | |
| A. | Compound of Example No. 12 | 25.00 |
| | Methyl cellulose | 0.3 |
| | Silica Aerogel | 1.5 |
| | Sodium lignosulfonate | 3.5 |
| | Sodium N-methyl-N-oleyl taurate | 2.0 |
| | Water | 67.7 |
| | | 100.00 |
| B. | Compound of Example No. 4 | 45.0 |
| | Methyl cellulose | 0.3 |
| | Silica aerogel | 1.5 |
| | Sodium lignosulfonate | 3.5 |
| | Sodium N-methyl-N-oleyl taurate | 2.0 |
| | Water | 47.7 |
| | | 100.00 |
| III. Wettable Powders | | |
| A. | Compound of Example No. 16 | 25.0 |
| | Sodium lignosulfonate | 3.0 |
| | Sodium N-methyl-N-oleyl-taurate | 1.0 |
| | Amorphous silica (synthetic) | 71.0 |
| | | 100.00 |
| B. | Compound of Example 20 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 6 | 10.0 |
| | Sodium lignosulfonate | 3.0 |
| | Sodium N-methyl-N-oleyl-taurate | 1.0 |
| | Kaolinite clay | 86.0 |
| | | 100.00 |
| IV. Dusts | | |
| A. | Compound of Example No. 11 | 1.0 |
| | Attapulgite clay | 98.0 |
| | | 100.00 |
| B. | Compound of Example No. 8 | 60.0 |

-continued

| | | Weight Percent |
|---|---|---|
| | Montmorillonite | 40.0 |
| | | 100.00 |
| C. | Compound of Example No. 19 | 30.0 |
| | Ethylene glycol | 1.0 |
| | Bentonite | 69.0 |
| | | 100.00 |
| D. | Compound of Example No. 13 | 1.0 |
| | Diatomaceous earth | 99.0 |
| | | 100.00 |
| V. Granules | | |
| A. | Compound of Example No. 6 | 15.0 |
| | Granular attapulgite (20/40 mesh) | 85.0 |
| | | 100.00 |
| B. | Compound of Example No. 7 | 30.0 |
| | Diatomaceous earth (20/40) | 70.0 |
| | | 100.00 |
| C. | Compound of Example No. 8 | 1.0 |
| | Ethylene glycol | 5.0 |
| | Methylene blue | 0.1 |
| | Pyrophyllite | 93.9 |
| | | 100.00 |
| D. | Compound of Example No. 9 | 5.0 |
| | Pyrophyllite (20/40) | 95.0 |
| | | 100.00 |

When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. 4-Chloro-5-methoxy-3-pyridazine.
2. 3-(4-Chloro-3,5-dimethylphenoxy)-5-methoxypyridazine.

3. 5-Methoxy-3-pyridazine.

4. A herbicidal composition comprising a carrier and a herbicidally effective amount of a compound selected from the group consisting of 4-chloro-5-methoxy-3-pyridazine, 3-(4-chloro-3,5-dimethylphenoxy)-5-methoxypyridazine, and 5-methoxy-3-pyridazine.

5. A herbicidal method comprising applying to a plant locus a herbicidally effective amount of a compound selected from the group consisting of 4-chloro-5-methoxy-3-pyridazine, 3-(4-chloro-3,5-dimethylphenoxy)-5-methoxypyridazine, and 5-methoxy-3-pyridazine.

* * * * *